US006565543B1

(12) United States Patent
Buehler

(10) Patent No.: US 6,565,543 B1
(45) **Date of Patent: *May 20, 2003**

(54) DROP DISPENSERS

(75) Inventor: John D. Buehler, Bridgeton, NJ (US)

(73) Assignee: Comar, Inc., Buena, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/671,642

(22) Filed: Sep. 28, 2000

Related U.S. Application Data

(63) Continuation-in-part of application No. 09/246,936, filed on Feb. 9, 1999, now Pat. No. 6,168,581.

(51) Int. Cl.$^{7}$ .............................................. A61M 35/00

(52) U.S. Cl. .......................... 604/295; 604/298; 222/42

(58) Field of Search ................................ 604/295, 298; 222/42; 128/204.18, 205.11, 205.24

(56) References Cited

U.S. PATENT DOCUMENTS 4,568,004 A * 2/1986 Goncalves .................. 222/207
4,776,495 A * 10/1988 Vignot ........................ 222/206
5,431,314 A * 7/1995 Bonnelye et al. ........... 222/420
5,549,224 A * 8/1996 Wu et al. .................... 222/158
5,588,559 A * 12/1996 Vallet Mas et al. ......... 210/445
6,129,248 A * 10/2000 Hagele ....................... 222/420

* cited by examiner

*Primary Examiner*—Glenn K. Dawson
*Assistant Examiner*—Michael Mendoza
(74) *Attorney, Agent, or Firm*—Eugene E. Renz, Jr.

(57) ABSTRACT

A drop dispenser having a sleeve carrying a closure and resilient dosage receiving fitting. The sleeve is treadably mounted on a fluid containing container having a nipple thereon. The closure on the sleeve has a configuration corresponding to the configuration of the nipple for sealing the nipple in the closed position. The fitting is filled with fluid from the container by turning the sleeve in a direction away from the closed position on the nipple to an open position to thereby establish fluid communication between the container and fitting. The fluid is dispensed from the fitting by squeezing the fitting after the closure has been returned to the closed position on the nipple, thereby preventing fluid from flowing from the resilient fitting back into the container. Cooperating stop members are provided between the sleeve and bottle neck to limit the movement of the sleeve relative to the bottle neck.

14 Claims, 2 Drawing Sheets

DROP DISPENSERS

This application claims the benefit of and is a continuation-in-part of U.S. patent application Ser. No. 09/246,936 filed Feb. 9, 1999 now U.S. Pat. No. 6,168,581.

BACKGROUND OF THE INVENTION

Various drop dispensers have been proposed wherein a desired or measured amount of fluid is discharged to a resilient end fitting mounted on the outlet of a container containing the fluid, whereby the measured amount of fluid is dispensed by squeezing the resilient end fitting. While these drop dispensers have been generally satisfactory for their intended purpose, they have been characterized by a certain disadvantage in that when squeezing the resilient end fitting to dispense the measured amount of fluid, such as a medicant, a certain amount of the fluid returns to the container, thereby preventing the user from receiving an exact dose of the dispensed fluid.

After considerable research and experimentation, the drop dispenser of the present invention has been devised to overcome the problem of the fluid returning to the container when the resilient end fitting is squeezed to dispense the fluid.

SUMMARY OF THE INVENTION

The drop dispenser of the present invention comprises, essentially, a squeeze bottle having a nozzle or nipple on the outlet of the bottle neck. A sleeve is threadably mounted on the bottle neck, and an apertured closure carrying a spike is mounted on the sleeve. The spike is adapted to seal the nozzle when the sleeve is turned to the closed position. A resilient dosage-receiving fitting having a reservoir compartment or chamber is also mounted on the sleeve and is filled from the bottle by turning the sleeve a limited distance in a direction to move the spiked closure away from the sealed position on the nozzle. A dosage is delivered to the resilient fitting chamber by squeezing the bottle, and the sleeve is turned in the opposite direction to move the spike to the closed or sealed position on the bottle nozzle. The dosage is then dispensed through an outlet aperture in the resilient fitting by squeezing the fitting.

Cooperating stop members are provided between the sleeve and bottle neck to limit the movement of the sleeve relative to the bottle neck.

DETAILED DESCRIPTION OF THE PREFERRED EMBODIMENT

Figure 1:
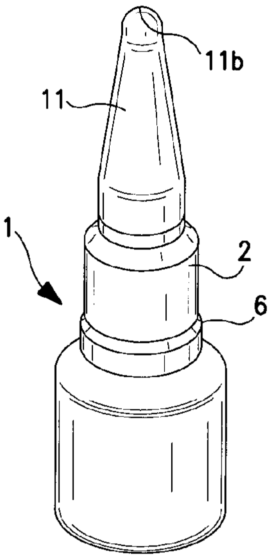
FIG. 1 is a perspective view of the drop dispenser of the present invention mounted on a bottle.
Figure 3:
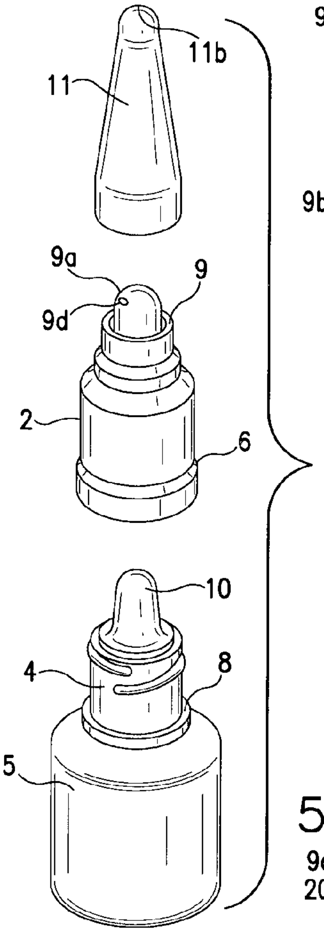
FIG. 3 is an exploded view showing the components of the assembly shown in FIG. 2.
Figure 2:
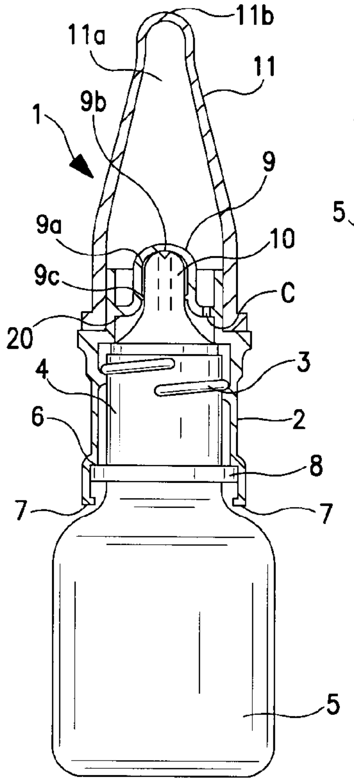
FIG. 2 is a side elevational view, partly in section, of the bottle and associated nozzle showing the drop dispenser in the closed position.

Referring to the drawings and, more particularly to FIGS. 1, 2 and 3, the drop dispenser (1) of the present invention comprises an open-end sleeve (2), threadably connected as at (3) to the neck (4) of a squeezable container (5) containing a fluid, such as a medicant. The lower end portion of the sleeve (2) is provided with a shoulder (6) and a plurality of radially inwardly extending hooks (7) spaced axially from the shoulder (6). The shoulder (6) and hooks (7), respectively, engage the upper and lower surfaces of a collar (8) integral with the container neck (4) when the sleeve (2) is turned relative thereto, to be described more fully hereinafter.

The upper end portion of the sleeve (2) is provided with an integral closure (9) having a tubular medial portion and arcuate end wall (9*a*) conforming to the arcuate tubular configuration of a nozzle or nipple (10) connected to the open end of the container (5). A depending protuberance or spike (9*b*), integral with the arcuate portion (9*a*) of the closure (9), is adapted to seal the conventional outlet of the nipple (10) when the sleeve (2) has been turned to the closed position as shown in FIG. 2. To further seal the connection between the closure (9) and nipple (10), an annular inwardly extending bead (9*c*) is formed on the inner surface of the arcuate portion (9*a*) of the closure (9) and engages the outer surface of the nipple (10).

Figure 5:
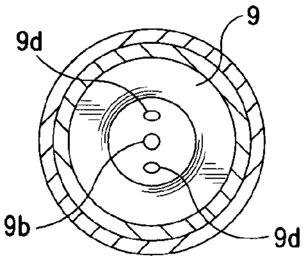
FIG. 5 is a view taken along line 5—5 of FIG. 4.

As will be seen in FIG. 5, the end wall of the closure (9) is provided with an aperture (9*d*) on each side of the spike (9*b*).

Figure 4:
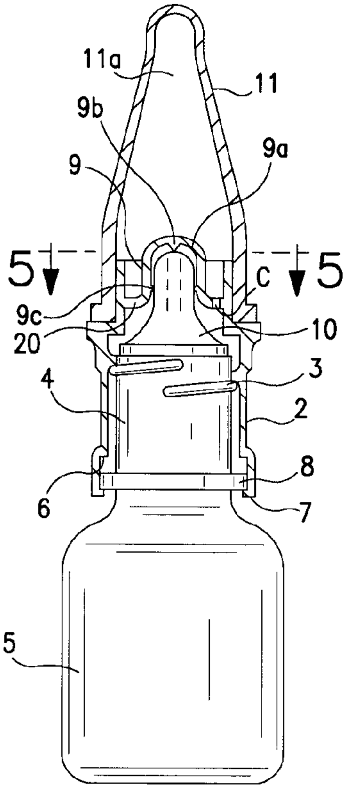
FIG. 4 is a side elevational view, partly in section, similar to FIG. 2, but showing the drop dispenser in the open position, and illustrating one embodiment of the stop member.

To complete the structure of the drop dispenser, a resilient squeezable fitting (11), having a dosage receiving chamber (11*a*), is mounted on the end of the sleeve (2) by a fraction fit so that the fitting (11) can be removed therefrom when desired for cleaning. In the operation of the drop dispenser (1) of the present invention, the sleeve (2) is first turned from the closed position as shown in FIG. 2, to the open position as shown in FIG. 4. The container (5) is then squeezed to cause the fluid to flow therefrom through the nipple (10) and apertures (9*d*) in the closure (9) into the dosage receiving chamber (11*a*) of the fitting (11). After the desired dosage is received in the fitting (11), the sleeve (2) is turned in the opposite direction to close and seal the nipple (10) as shown in FIG. 2. The fitting (11) is then squeezed to dispense the dosage through an aperture (11*b*) provided in the end of the fitting (11). The radial wall 20 of the closure (9) is provided with vent means in the form of an axially extending channel C permitting flow of airform the reservoir chamber (11*a*) during a filling cycle when the closure (9) is in an open position. The axially extending channel C defines vent means permitting flow of air from the reservoir chamber (11*a*) during a filling cycle when the closure (9) is in an open position. In the operation of the drop dispenser (1) of the present invention, the sleeve (2) is first turned from the closed position as shown in FIG. 2, to the open position as shown in FIG. 4. The container (5) is then squeezed to cause the fluid to flow therefrom through the nipple (10) and apertures (9*d*) in the closure (9) into the dosage receiving chamber (11*a*) of the fitting (11). After the desired dosage is received in the fitting (11), the sleeve (2) is turned in the opposite direction to close and seal the nipple (10) as shown in FIG. 2. The fitting (11) is then squeezed to dispense the dosage through an aperture (11*b*) provided in the end of the fitting (11).

While the spike (9*b*) closes the aperture in the nipple (10) when the sleeve (2) has been turned to the closed position, the bead (9*c*) engages the outer surface of the nipple (10) at all times and provides a seal to prevent fluid in the container (5) from flowing into the interior of the sleeve (2) between the closure (9) and the container neck (4), to thereby prevent the thread connection from becoming contaminated.

The turning of the sleeve (2) to the open position is limited by the hooks (7) on the lower end of the sleeve (2) engaging the lower surface of the collar (8), as shown in FIG. 4; and the turning of the sleeve (2) to the closed position, as shown in FIG. 2 is limited by the shoulder (6) on the lower portion of the sleeve (2) engaging the upper surface of the collar (8). The construction and arrangement of the shoulder (6), hooks (7), collar (8), and thread connection (3) limits the turning of the sleeve (2) to approximately ½ a turn.

Figure 6:
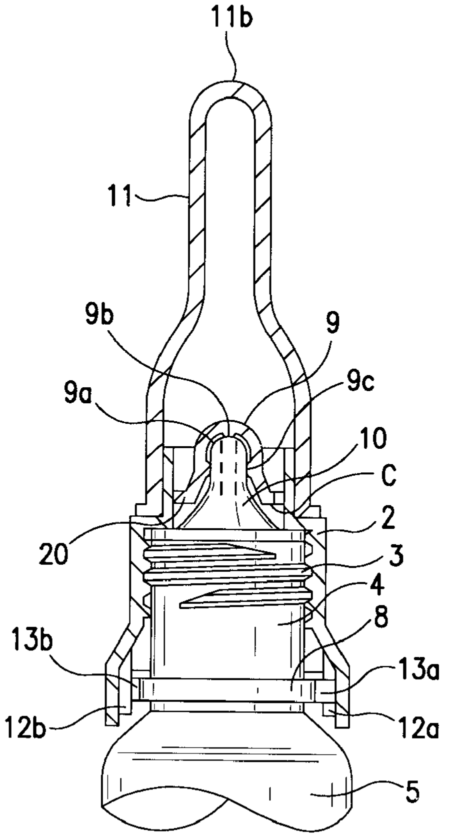
FIGS. 6 and 7 are views similar to FIGS. 2 and 4, respectively, but illustrating another embodiment of the stop member.
Figure 7:
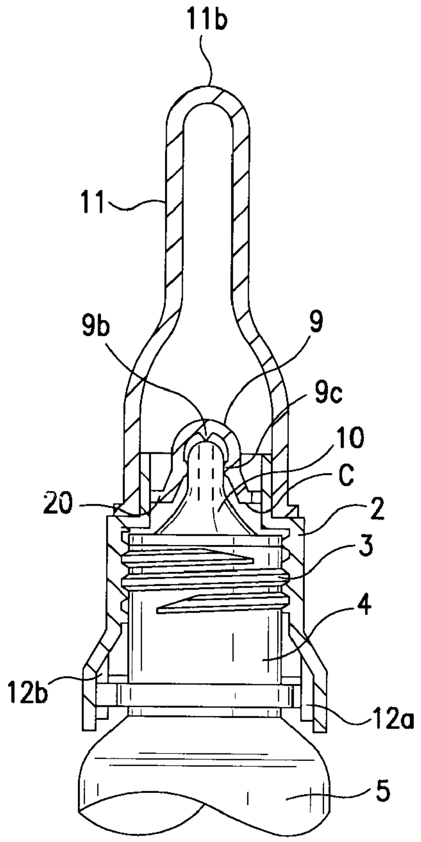
Figure 8:
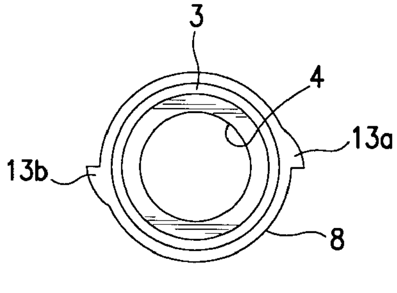
FIG. 8 is a top plan view of the bottle neck shown in FIGS. 6 and 7.

Another embodiment of a stop for limiting the turning of the sleeve (2) is illustrated in FIGS. 6, 7, and 8, wherein a pair of diametrically opposed radially inwardly extending fingers (12*a*) and (12*b*) are integral with the inner surface of the sleeve (2) at the lower end portion thereof, and a pair of diametrically opposed radially outwardly extending tabs (13*a*, 13*b*) are integral with the collar (8). By the construction and arrangement of the thread connection (3), fingers (12*a*, 12*b*), and tabs (13*a*, 13*b*), the turning of the sleeve (2) to the open position is limited by the finger (12*a*) engaging the tab (13*a*) as shown in FIG. 7, and the turning of the sleeve (2) to the closed position, as shown in FIG. 6, is limited by the finger (12*b*) engaging the tab (13*b*). The turning of the sleeve (2) in this embodiment is limited to approximately ⅜ of a turn.

From the above description, it will be appreciated by those skilled in the art that the drop dispenser (1) of the present invention is an improvement over previous dispensers in that fluid is prevented from returning to the supply container (5) when the resilient fitting (11) is squeezed, and the spike (9*b*) and annular bead (9*c*) provide a seal between the closure (9) and nozzle (10) on the container (2) when the closure (9) is in the closed position, and the annular bead (9*c*) also provides a seal when the closure (9) is moved to the open position to thereby prevent fluid from the container (5) from flowing into the intenor of the sleeve (2) between the closure (9) and container neck to thereby prevent the thread connection (3) from becoming contaminated.

It is to be understood that the form of the invention herewith shown and described is to be taken as a preferred example of the same, and that various changes in the shape, size, and arrangement of parts may be resorted to, without departing from, the spirit of the invention or scope of the subjoined claims.

What is claimed is:

1. A drop dispenser for use on a container for liquid products having a threaded open end neck portion, a nipple having a discharge opening mounted on the open end of the neck and a circumferentially extending radially outwardly projecting collar spaced downwardly from the threaded portion of the neck, said drop dispenser comprising an elongated sleeve member having internal threads for cooperating with the threaded portion of the container and a dosing valve overlying and conforming generally in shape to the nipple portion of the container and a dispensing tip having a discharge opening mounted over the dosing valve and spaced therefrom to define a reservoir chamber, said dosing valve having a protruberance engageable with the discharge port in the nipple in a closed position and having seal means engaging the nipple in the closed position and means at the lower end of the sleeve cooperatively engaging the collar to limit axial displacement of the sleeve member relative to the container, whereby the reservoir chamber is filled with fluid from the container by turning the sleeve in a direction to move the closure away from a closed position of the nipple to an open position relative thereto, to thereby establish fluid communication between the container and the reservoir chamber, the fluid being dispensed through the fitting outlet from the reservoir chamber by squeezing the resilient fitting after the sleeve has been turned in a direction to move the closure to the closed position on the nipple thereby preventing the fluid from flowing from the resilient fitting back into the container and vent means in the closure to permit venting the reservoir chamber during the filling process when the closure is in the open position.

2. A drop dispenser in accordance with claim 1, wherein the container is a squeezable bottle.

3. A drop dispenser in accordance with claim 1, wherein the fluid is a medicament.

4. A drop dispenser in accordance with claim 1, wherein the closure has a configuration corresponding to the configuration of said nipple.

5. A drop dispenser in accordance with claim 4, wherein the closure has a tubular portion having an arcuate end wall.

6. A drop dispenser in accordance with claim 5, wherein a depending spike is integral with the arcuate end wall of said closure and insertable into the nipple outlet when the closure is moved to the closed position.

7. A drop dispenser in accordance with claim 6, wherein at least one aperture is provided in the closure arcuate end wall offset from said spike.

8. A drop dispenser in accordance with claim 5, wherein an annular bead is formed on an inner surface of said closure tubular portion engaging an outer surface on the tubular portion of said nipple to thereby provide a seal between the closure and nipple.

9. A drop dispenser in accordance with claim 1, wherein cooperating stop members are provided on the sleeve and container neck to limit the turning of the sleeve on the container neck.

10. A drop dispenser in accordance with claim 9, wherein the stop member on the sleeve comprises a shoulder provided on the sleeve and a plurality of radially inwardly extending hooks integral with the sleeve and spaced axially from the shoulder, the cooperating stop member on the container neck comprising a collar integral with the container neck.

11. A drop dispenser in accordance with claim 9, wherein the stop member on the sleeve comprises a pair of diametrically opposed radially inwardly extending fingers integral with an inner surface of said sleeve, the stop member on the container neck having a pair of diametrically opposed radially outwardly extending tabs integral with the container neck.

12. In combination, a drop dispenser for use on a container for liquid products having a threaded open end neck portion, a nipple having a discharge opening mounted on the open end of the neck and a circumferentially extending radially outwardly projecting collar spaced downwardly from the threaded portion of the neck, said drop dispenser comprising an elongated sleeve member having internal threads for cooperating with the threaded portion of the container and a dosing valve overlying and conforming generally in shape to the nipple portion of the container and a dispensing tip having a discharge opening mounted over the dosing valve and spaced therefrom to define a reservoir chamber, said dosing valve having a protruberance engageable with the discharge port in the nipple in a closed position and having seal means engaging the nipple in the closed position and means at the lower end of the sleeve cooperatively engaging the collar to limit axial displacement of the sleeve member relative to the container, whereby the reservoir chamber is filled with fluid from the container by turning the sleeve in a direction to move the closure away from a closed position of the nipple to an open position relative thereto, to thereby establish fluid communication between the container and the reservoir chamber, the fluid being dispensed through the fitting outlet from the reservoir chamber by squeezing the resilient fitting after the sleeve has been turned in a direction to move the closure to the closed position on the nipple thereby preventing the fluid from flowing from the resilient fitting back into the container.

13. A drop dispenser for use on a container for a fluid having a threaded open end neck portion, and a nipple having an outlet mounted on the open end of the neck; said drop dispenser comprising a sleeve threadably mounted on the neck portion and of said container, a closure secured to said sleeve for closing the outlet of the nipple, and a resilient dosage-receiving fitting mounted on said sleeve downstream from said closure overlying said closure and spaced therefrom to define a reservoir chamber and having an outlet, whereby the reservoir chamber is filled with fluid from the container by turning the sleeve in a direction to move the closure away from a closed position on the nipple to an open position relative thereto, to thereby establish fluid communication between the container and the reservoir chamber, the fluid being dispensed through the fitting outlet from the reservoir chamber by squeezing the resilient fitting after the sleeve has been turned in a direction to move the closure to the closed position on the nipple thereby preventing the fluid from flowing from the resilient fitting back into the container and vent means in the closure to permit venting the reservoir chamber during the filling process when the closure is in the open position.

14. A drop dispenser for use on a container for liquid products having a threaded open end neck portion, a nipple having a discharge opening mounted on the open end of the neck and a circumferentially extending radially outwardly projecting collar spaced downwardly from the threaded portion of the neck, said drop dispenser comprising an elongated sleeve member having internal threads for cooperating with the threaded portion of the container and a dosing valve overlying and conforming generally in shape to the nipple portion of the container and a dispensing tip having a discharge opening mounted over the dosing valve and spaced therefrom to define a reservoir chamber, said dosing valve having a protruberance engageable with the discharge port in the nipple in a closed position and having seal means engaging the nipple in the closed position and means at the lower end of the sleeve cooperatively engaging the collar to limit axial displacement of the sleeve member relative to the container, whereby the reservoir chamber is filled with fluid from the container by turning the sleeve in a direction to move the closure away from a closed position of the nipple to an open position relative thereto, to thereby establish fluid communication between the container and the reservoir chamber, the fluid being dispensed through the fitting outlet from the reservoir chamber by squeezing the resilient fitting after the sleeve has been turned in a direction to move the closure to the closed position on the nipple thereby preventing the fluid from flowing from the resilient fitting back into the container.

* * * * *